United States Patent [19]
Cook

[11] Patent Number: 6,086,892
[45] Date of Patent: Jul. 11, 2000

[54] POULTRY VACCINE

[75] Inventor: Jane Kathleen Alexandra Cook, Cambs, United Kingdom

[73] Assignee: Akzo Nobel N.V., Arnhem, Netherlands

[21] Appl. No.: 09/048,256

[22] Filed: Mar. 26, 1998

Related U.S. Application Data

[62] Division of application No. 08/574,561, Dec. 14, 1995, Pat. No. 5,750,113, which is a continuation of application No. 08/282,689, Aug. 1, 1994, abandoned.

[30] Foreign Application Priority Data

Jul. 30, 1993 [EP] European Pat. Off. .............. 93306033

[51] Int. Cl.[7] ........................ A61K 39/215; A61K 39/12; A61K 39/295; A61K 39/155; C12N 7/00
[52] U.S. Cl. ..................... 424/222.1; 424/184.1; 424/202.1; 424/211.1; 424/816; 435/240.1; 435/235.1; 435/239; 435/948; 435/236; 435/237
[58] Field of Search .............................. 424/222.1, 184.1, 424/202.1, 211.1, 816; 435/240.1, 235.1, 239, 948, 236, 237

[56] References Cited

U.S. PATENT DOCUMENTS 4,645,665  2/1987  Apontoweil et al. .
4,692,410  9/1987  Apontoweil et al. .
4,751,079  6/1988  Burger et al. .
4,761,282  8/1988  Apontoweil et al. .
4,824,668  4/1989  Melchior et al. .
4,867,975  9/1989  Gelb .
5,032,520  7/1991  Binns et al. .
5,069,902  12/1991  Cook et al. .
5,750,113  5/1998  Cook .

OTHER PUBLICATIONS

Martins et al., *Avian Diseases*, 35:47–475, 1991.
Winterfield et al., *Avian Diseases*, 20(2):369–374, 1975.
Raggi et al., *Avian Diseases*, 19(2):323–333, 1974.
Cavanaugh et al., *Avian Pathology*, 21:33–43, 1992.
Gelb et al., *Avian Diseases*, 40(3): 605–612, 1996.
Wang et al., *Virology*, 192:710–716, 1993.
Klieve et al., *Avian Pathology*, 19:305–312, 1990.
Davelaar et al., *Vet Quarterly*, 6(3):114–120, 1984.
Yachida et al., *Zbl. Vet. Med. B.*, 32:736–743, 1985.
Tarcha et al., *Acta. Vet. Hungarica*, 38(4):287–298, 1990.
Capua et al., *J. Vet. Med. B.*, 41:83–89, 1994.
Klieve et al., *Avian Pathology*, 17(4):829–839, 1988.
Gough et al., *The Veterinary Record*, 103:493–494, 1992.
Parsons et al., *The Veterinary Record*, 131:408–411, 1992.
Gelb et al., *Avian Diseases*, 35:82–87, 1991.
Kusters et al., *J. Gen. Virology*, 68:343–352, 1987.
Peters et al., *Res. in Vet. Sci.*, 26:38–40, 1979.
Cook, *Avian Pathology*, 13:733–741, 1984.
Darbyshire et al., *Archives of Virol.*, 61:227–238, 1979.

*Primary Examiner*—Nita Minnifield
*Attorney, Agent, or Firm*—Mary E. Gormley

[57] ABSTRACT

This invention relates to a novel infectious bronchitis virus (IBV) serotype and to attenuated IBV strains derived therefrom, and also to live or inactivated vaccines made using such IB virus. This invention also relates to a method for protecting poultry against IBV using these vaccines.

8 Claims, No Drawings

POULTRY VACCINE

This is a division of application Ser. No. 08/574,561, filed Dec. 14, 1995 U.S. Pat. No. 5,750,113, which is a continuation of U.S. Ser. No. 08/282,689, filed Aug. 1, 1994 now abandoned.

The present invention relates to a new infectious bronchitis virus serotype, to attenuated infectious bronchitis virus strains derived from this new serotype and to a live vaccine, for use in immunizing poultry, which vaccine contains the attenuated strain of infectious bronchitis virus. The invention also relates to an inactivated vaccine containing either the new serotype which has been inactivated, or an inactivated attenuated strain derived therefrom. The invention is also concerned with a process for the preparation of live infectious bronchitis vaccines.

Infectious bronchitis virus (IBV) is a member of the genus *coronavirus* of the family Coronaviridae. The virus is usually about 80–100 nm in size, being round with projecting 20 nm spikes. IBV is the causative agent of an acute, highly contagious disease in chickens of all ages, affecting the respiratory, reproductive and renal systems.

IBV has been reported in all countries where an intensive poultry industry has been developed. Young chickens up to 4 weeks of age are most susceptible to respiratory disease, infection leading to high rates of morbidity and to mortality resulting from secondary bacterial infection. Infection in layers results in a drop in egg production, or failure to lay at full potential, together with an increase in the number of down-graded eggs with thin, misshapen, rough and soft-shells produced. Although layers usually recover from the disease, their egg production rarely returns to pre-infection levels. Thus infection of flocks of chickens with IBV can have a serious economic effect.

Spackman and Cameron (*Veterinary Record*, (1983), 113, 354–355.) isolated IBV from pheasants with a history of respiratory signs and aberrant egg production. This disease problem in pheasants was successfully controlled by the use of oil-based inactivated IBV vaccine. Thus the term poultry, as used herein, is intended to embrace chickens, pheasants and any other domesticated bird serving as a source of eggs or meat and that are susceptible to infection by IBV.

Initially, most of the virulent IBV strains isolated were of the Masachussetts serotype, and for many years this was thought to be the only serotype of IBV. However, it is now known that different serotypes appear to be present in distinct geographical areas; for example, Arkansas 99 (Johnson et al., *Avian Dis.*,(1973),17, 518–523) has been isolated in the U.S.A., whilst D274 serotype (Davelaar et al., *Proc. World Vet. Poultry Assoc.*, Oslo, 1981,p.44) has not been isolated in the U.S.A.

The only practical means of preventing infectious bronchitis in poultry is to vaccinate against the infection. Two main types of vaccine are available and they are attenuated and inactivated.

Reports of new serotypes have been numerous over the years in many countries. More recently, for example, Gough et al., in *The Veterinary Record*, (1992). 130, 493–494, reported a possible new strain of IBV in infected domestic fowl in Great Britain. They showed that the new strain' of IBV had antigenic differences from M41 and the Dutch variants from which many current IBV vaccines are derived.

In addition, Parsons et al., in *The Veterinary Record*, (1992), 131, 408–411 also described isolates of IBV which "were serologically distinct from isolates previously described and capable of causing characteristic infectious bronchitis-like respiratory infection in young chickens."

It is well known that many new serotypes will not cause infectious bronchitis in birds which have been vaccinated. However, a new serotype of IBV has now been isolated which has been found to cause overt infection in vaccinated chickens.

Neither of these two recent publications describe the serotype or strain in such a manner as to enable the skilled person in the art to be able to identify an isolate of IBV as belonging to this new serotype.

According to one aspect of the invention there is provided a novel infectious bronchitis virus serotype which has been isolated from chickens and deposited on Jul. 6, 1993 with the European Collection of Animal Cell Cultures, Porton Down, United Kingdom, under the Budapest Treaty, and designated accession no. V93070612, and/or an infectious bronchitis strain which is cross-neutralised significantly by antisera raised in chickens against said deposited strain.

According to a second aspect of the invention there is provided an IBV strain belonging to a new serotype, said new serotype being characterised by the deposit referred to above, said IBV strain being cross-neutralised significantly by antisera raised in chickens against said deposited strain.

The novel IBV serotype of the present invention, hereinafter referred to as 4/91, was isolated from chickens which had previously been vaccinated with a commercially available inactivated bivalent infectious bronchitis vaccine, and which exhibited the characteristic symptoms of IBV infection. Samples of tissue from the trachea and caecal tonsils from dead affected birds were taken, homogenised and passaged in chicken embryo tracheal organ cultures. After the second or third organ culture passage, virus particles with typical coronavirus morphology were observed by electron microscopy in organ culture supernatants.

In addition to identification using the electron microscope, the isolated virus was found to possess nucleic acid of the RNA type. Using an ELISA it was demonstrated that the viruses contained antigen in common with known avian coronavirus, e.g. IBV reference strain M41. The virus was also identified as being IBV by performing the polymerase chain reaction with viral RNA using universal primers for IBV according to Lin, Z., *Archives of Virology*, (1991), 116, 19.

Serum neutralisation tests were carried out in tracheal organ cultures. Monospecific antiserum to each of 41 known serotypes was prepared in chickens and used to test the novel serotype 4/91. Table 1 summarises the results of the virus neutralisation tests. The isolated virus was also found to spontaneously hemagglutinate chicken red blood cells and this hemagglutination could be inhibited by specific antiserum.

Cross neutralisation tests were carried out between the novel IBV serotype 4/91 and seven other IBV serotypes. This was carried out in tracheal organ cultures. Each monospecific antiserum being tested at a range of doubling dilutions against log10 2.0 CD50 of each virus (CD50= median ciliostatic dose). The results are presented in Table 2.

Table 3 shows the results of analysing the data according to the method of Archetti,I. and Horsfall, F. L.,*J. Exyt. Med.*, (1950), 92, 441–462, which expresses the relationship (r) between strains as a percentage. Applying this method to IB neutralisation tests in embryos, it has been suggested (Locher et al., *Berliner und Munchener Tierarztliche Wochenschrift*, (1983) , 96, 269–274) that r values greater than 50 indicate close relationships, values between 25 and 50 indicate a lower degree of relationship, whilst values below 25 indicate little relationship.

Thus the term "cross-neutralised significantly" means that, using the method of Archetti and Horsfall, an IBV strain with an 'r' value of greater than 50 may be considered to be closely related to the novel serotype of the present invention.

The present invention also relates to an attenuated infectious bronchitis virus, that is the IBV serotype 4/91, or an IBV strain belonging to the new serotype, as defined above, which is attenuated. Such an attenuated IBV is obtainable by passaging the IBV in a culture on a suitable medium a sufficient number of times to reduce its pathogenicity whilst retaining its immunogenicity. Preferably the IBV is passaged at least 30 times.

An attenuated strain of the novel IBV serotype has been deposited on Jul. 6, 1993 with the European Collection of Animal Cell Cultures, Porton Down, UK,under the Budapest Treaty, under accession no. V93070611.

To attenuate the novel IBV serotype of the present invention the virus may be passaged in embryonated eggs. Inoculation of the eggs can be via the allantoic cavity, chorioallantoic membrane, yolk sac, amniotic cavity or even direct into the embryo. The virus can be passaged at regular intervals of from 7 hours up to 4 days. More usually passaging takes place between 16 to 36 hours, preferably every 24 hours.

Alternatively, attenuation may be achieved by passaging the virus in avian cell culture, such as chick embryo kidney cells.

The attenuated IBV prepared as described above, or the deposited attenuated strain, may be used in the preparation of a live vaccine. Thus according to a further aspect of the present invention there is provided a live infectious bronchitis vaccine for use in immunizing poultry said vaccine derived from the IBV described above.

According to another aspect of the invention there is provided a process for the preparation of a live infectious bronchitis vaccine which comprises passaging the novel IBV serotype, or strain as hereinbefore described, in a culture on a suitable medium a sufficient number of times to reduce its pathogenicity whilst retaining its immunogenicity and processing the material harvested to produce a vaccine. Preferably the virus is passaged at least 30 times.

The present invention also relates to the use of an attenuated infectious bronchitis virus strain, as hereinbefore described, for the preparation of a vaccine for use in vaccinating poultry against IBV.

Such live vaccines may be administered by eye drop, nose drop, in drinking water, or by spraying the birds, at any age from one day old up to point of lay (about 18 weeks). The dosage used is preferably in the range of log10 3.0 to log10 7.0 EID50 per bird, preferably between log10 4.0 and log10 5.0 EID50 per bird.

Such an attenuated IB vaccine may be administered in combination with other live avian vaccines, for example Newcastle Disease Virus (NDV), Mareks Disease Virus (MDV), Infectious Bursal Disease (IBD), reovirus, Avian Encephalomyelitis, Chicken Anaemia Agent (CAA) and other IBV serotypes.

Alternatively, the novel IBV serotype according to the invention and/or the novel attenuated IBV strain described above may be presented as an inactivated vaccine. According to yet a further aspect of the invention there is provided an inactivated infectious bronchitis vaccine for use in immunizing poultry, which vaccine contains IBV which is derived from the novel IBV serotype described above, the IBV strain as hereinbefore defined or the attenuated IBV strain described above.

For both live and inactivated vaccine production the IBV is usually grown in embryonated specific pathogen free (SPF) chicken eggs. After harvesting, the virus may be inactivated, for use in a killed vaccine, using for example formaldehyde or β-propiolactone.

After inactivation and, if necessary, adjusting of the pH and neutralising of the inactivating agent, the inactivated virus may be mixed with an adjuvant. The adjuvant can be aluminium hydroxide or a composition consisting of mineral oil (e.g. Marcol 82) or a plant oil and one or more emulsifiers like Tween 80 and Span 80.

Inactivated vaccines are usually administered by subcutaneous or intramuscular injection at between 10 to 20 weeks of age. Inactivated vaccine may contain the antigenic equivalent of log10 5.0 to log10 8.0 EID50 per bird dose, preferably log10 6.0 to log10 8.0 EID50.

Such an inactivated IBV vaccine may be administered in combination with other inactivated avian vaccines, for example NDV, CAA, Egg Drop Syndrome 1976 and other IBV serotypes.

According to yet a further aspect of the invention there is provided a method for protecting poultry against IBV comprising administering a vaccine as hereinbefore described to susceptible birds.

The invention is illustrated by the following examples.

EXAMPLE 1

Isolation of Infectious Bronchitis Virus

Samples of trachea, kidney and caecal tonsils were taken from dead birds from flocks manifesting the clinical symptoms of infection with IBV. The tissue samples were homogenised in Eagle's serum free medium, containing penicillin and streptomycin, to give 10% (w/v) suspension.

After centrifugation at 1, 500 g for 15 min., 0.1 ml of supernatant was inoculated into each of 10 drained tracheal organ cultures (TOC). After 1 hr. adsorption at 37° C., 0.5 ml of Eagle's serum free medium was added to each culture. The TOC were incubated at 37° C. on a roller drum and examined daily for ciliostasis. Up to three 'blind' passages were carried out before a sample was discarded as negative.

IBV was indicated in samples where ciliostasis of the TOC was observed. Supernatants of 'positive' samples were checked for absence of haemagglutination (to ensure freedom from Newcastle Disease virus), then their identity as IB was confirmed by serological analysis.

An ELISA assay was used to characterise further the isolates (see Mockett, A. P. A. and Cook, J. K. A., *Avian Pathology*, (1986), 15, 437.). Antiserum was raised to serotype 4/91 in specific pathogen free Rhode Island red chickens inoculated intranasally and bled four weeks later. The monospecific antiserum raised to isolate 4/91 was shown to react to a titre of log2 13.0 in the ELISA test, using plates coated with the M41 strain of IBV, evidence that the isolates were infectious bronchitis virus.

EXAMPLE 2

Attenuation of IBV Strain 4/91

SPF white leghorn embryonated eggs, used throughout at between 8 and 11 days of preincubation, were initially inoculated with 0.1 ml of pathogenic IBV 4/91 containing log10 6.4 CD50/ml of virus via the allantoic cavity and incubated at 37° C. for 24 hours. The allantoic fluid of half the embryos per group was harvested at the appointed time. The remaining embryonated eggs were incubated until 17–18 days old when they are examined for abnormalities indicative of IBV infection.

The harvested allantoic fluid, at appropriate dilution, was inoculated (0.1 ml) into the allantoic cavity of 10 embryos and harvested, as above, after 24 hours incubation. This passaging was carried out continuously until a sufficient number of passages (at least 30) had been achieved, with incubation times varying from 7 to 36 hours.

At selected passages, the allantoic fluid that had been harvested was titrated. A series of 10-fold dilutions of the fluid was prepared and assayed in either 9–11 day old embryos (inoculated via the allantoic route) or chicken embryo tracheal organ culture (TOC).

At intervals, the identity of the passaged virus was checked by means of a neutralisation test in TOC. Serial 2-fold dilutions of a known positive 4/91-specific chicken antiserum were mixed with an equal volume of embryo passaged IBV 4/91 (log10 2.0 CD50), incubated at 37° C. for 1 hour then inoculated into drained TOC (5/dilution). After a 1 hour adsorption period at 37° C. the TOC were overlaid (0.5 ml) with Eagles MEM containing hepes and α-methyl glucoside, then incubated at 37° C. and read 3 to 4 days later.

EXAMPLE 3
Preparation and Assessment of Attenuated IBV Vaccine

The attenuated IBV prepared as described in Example 2 was harvested from the allantoic cavity. The allantoic fluid was clarified by centrifugation and/or filtration and subsequently processed into a suitable vaccine preparation by methods known per se.

Groups of 9-day-old chicks were inoculated by eyedrop (0.1 ml) with either the attenuated IBV vaccine described above, or the Massachusetts vaccine (H120) or MA5 vaccine. At 30 days of age the chicks were challenged by inoculation with log10 4.6 CD50 of the IBV serotype 4/91 grown in tracheal organ culture. Seven days later 5 chicks/group were killed and their tracheas removed for the "ciliostasis" test (see Darbyshire, J. H. , Avian Pathology, (1980) , 9, 179–184.).

The chicks were killed by intravenous injection of Euthatal. Their tracheas were carefully removed and, using a scalpel, 10 rings carefully cut (3 from the top, 4 from the middle and 3 from the bottom). The 10 rings were examined under a low magnification and each scored on a scale from 0 (100% ciliary activity) to 4 (100% ciliostasis).
Results The results summarised in Table 4 show that at the one time tested (7 days post challenge) the attenuated IBV strain prepared in Example 2 protected well against a high homologous challenge. The two vaccine strains (H120 and MA5) gave poor protection against this high challenge; in each case 1/5 chickens was protected.

EXAMPLE 4
Preparation of Inactivated IB Vaccine

IBV was inoculated, via the allantoic cavity, into embryonated eggs which had been pre-incubated for between 8 and 11 days. After approximately 1–3 days incubation, the allantoic fluid was harvested, pooled, clarified by centrifugation and the virus was inactivated by the addition of formalin. The inactivation of the IB virus was confirmed by inoculation of 9 day old embryonated eggs via the allantoic cavity and subsequent examination of the embryos for signs of IB infection. An oil emulsion vaccine was then prepared using standard procedures. This was inoculated either subcutaneously or intramuscularly into groups of chickens, which may or may not have been 'primed' by earlier administration of live-attenuated IB vaccine. These chickens were bled at least 7 weeks later and their sera examined for IB specific antibodies by an ELISA.
Results 1). Unprimed, given inactivated vaccine, bled 7 weeks later.
   Mean titre(log2) 9.1
   Range log2 7.6–10.6
2) Primed, given inactivated vaccine, bled 7 weeks later.
   Mean titre(log2) 12.6
   Range log2 11.6–13.6

TABLE 1

IB virus serotype 4/91 was tested in a
neutralisation test against monospecific antiserum
raised against each of the following IBV serotypes
In each case the neutralisation titre was <1:8

UK serotypes

A; B; C; D; F; F1; H; I; J; 690; 317; 183; 918; 225;
HV1-116; D41; VF70-861, Allen
Dutch D207; D3896; D3128; D212
Portugal 135355/82
Israel IBV-11
Germany 5423/86; 332/88; IBV-10
Italy 1767/84; Forli 1; Forli 2
Belgium

B-1486
USA

Massachusettes; Connecticut; Iowa 609, Iowa 97; Holte;
Gray; Arkansas; 632
South Africa

890/80; 145/86

TABLE 2

Cross neutralisation between IBV serotype 4/91 and other IBV serotypes
Virus (log$_{10}$ 2.0 CD$_{50}$)

| | UK | | | France | | | Morocco | Australia |
|---|---|---|---|---|---|---|---|---|
| Antiserum | 4/91 | 591 | E | CR84084 | CR84221 | CR88061 | G | T |
| 4/91 | 1600* | — | 11 | ND | — | 30 | 9 | — |
| UK 591 | 13 | 1000 | — | ND | ND | ND | — | — |
| UK-E | 46 | — | 6260 | — | 14 | — | — | — |
| Fr. 84084 | — | — | — | 720 | 10 | — | — | 15 |

TABLE 2-continued

Cross neutralisation between IBV serotype 4/91 and other IBV serotypes
Virus ($\log_{10}$ 2.0 $CD_{50}$)

|  |  | UK |  | France |  |  | Morocco | Australia |
|---|---|---|---|---|---|---|---|---|
| Antiserum | 4/91 | 591 | E | CR84084 | CR84221 | CR88061 | G | T |
| Fr. 84221 | 30 | ND | 70 | 42 | <u>3240</u> | 10 | — | 14 |
| Fr. 88061 | 10 | ND | — | — | — | <u>140</u> | 10 | — |
| Morocco G | 19 | — | — | — | — | — | <u>400</u> | — |
| Australia T | 20 | ND | 16 | 58 | 10 | ND | — | <u>1300</u> |

*Reciprocal antiserum titre (homologous reaction underlined)
— titre = <1:8
ND not done

TABLE 3

Results analysed by the method of Archetti and Horsfall (1950)
"r" values

|  | UK | | | France | | | Morocco | Australia |
|---|---|---|---|---|---|---|---|---|
|  | 4/91 | 591 | E | CR84084 | CR84221 | CR88061 | G | T |
| 4/91 | 100 | — | 2 | ND | — | 5 | — | — |
| UK 591 |  | 100 | — | ND | ND | ND | — | ND |
| UK-E |  |  | 100 | — | — | — | — | — |
| Fr. 84084 |  |  |  | 100 | — | — | — | 3 |
| Fr. 84221 |  |  |  |  | 100 | — | — | — |
| Fr. 88061 |  |  |  |  |  | 100 | — | ND |
| Morocco G |  |  |  |  |  |  | 100 | — |
| Australia T |  |  |  |  |  |  |  | 100 |

— = ≦1

TABLE 4

Ciliary activity score on tracheas of 5 birds killed 7 days
after challenge with the virulent strain of IBV 4/91
Original inoculum (3 weeks pre challenge)

|  | Attenuated 4/91 | H120 | MA5 |
|---|---|---|---|
|  | 1* | 5 | 6 |
|  | 1 | 16 | 18 |
|  | 2 | 21 | 20 |
|  | 2 | 31 | 22 |
|  | 5 | 40 | 40 |
| Total | 11 | 113 | 106 |
| Mean | 2.2 | 22.6 | 21.6 |

*Total score for 10 rings examined from each individual bird.

I claim:

1. A live attenuated infectious bronchitis vaccine for use in immunizing poultry comprising an immunogenically effective amount of an isolated IBV and a pharmaceutically acceptable carrier, said IBV being of the same serotype as that of the IBV strain 4/91 deposited at the European Collection of Animal Cell Cultures, Porton Down, UK, under accession no. V93070612 and wherein the IBV is cross-neutralized by antisera raised in chickens against said deposited IBV, to the extent that said IBV has an r value of greater than 50 by the method of Archetti and Horsfall.

2. An inactivated infectious bronchitis vaccine for use in immunizing poultry, comprising a pharmaceutically acceptable carrier and an immunogenically effective amount of an inactivated IBV which is the same serotype as that of IBV strain 4/91 deposited at the European Collection of Animal Cell Cultures, Porton Down, UK, under accession no. V93070612 and wherein the IBV is cross-neutralized by antisera raised in chickens against said deposited IBV, to the extent that said IBV has an r value of greater than 50 by the method of Archetti and Horsfall.

3. A process for the preparation of live infectious bronchitis vaccine, which comprises passaging an infectious bronchitis virus in a culture on a suitable medium for sufficient number of times to reduce its pathogenicity while retaining its immunogenicity, harvesting the attenuated virus and processing the harvested material to produce a vaccine comprising IBV and a pharmaceutically acceptable carrier, wherein the IBV is of the same serotype as that of IBV strain 4/91 deposited at the European Collection of Animal Cell Cultures, Porton Down, UK, under accession no. V93070612 and wherein the IBV is cross-neutralized by antisera raised in chickens against said deposited IBV, to the extent that said IBV has an r value of greater than 50 by the method of Archetti and Horsfall.

4. A process according to claim 3, wherein the IBV is passaged at least 30 times.

5. A method for protecting poultry against infectious bronchitis virus, comprising administering a vaccine according to claim 1 to susceptible birds.

6. A live attenuated infectious bronchitis vaccine according to claim 1, comprising additional live avian vaccine immunogens.

7. An inactivated infectious bronchitis vaccine according to claim 2, comprising additional inactivated avian vaccine immunogens.

8. A method for protecting poultry against infectious bronchitis virus, comprising administering a vaccine according to claim 2 to susceptible birds.

* * * * *